United States Patent [19]

Yamakawa et al.

[11] Patent Number: 5,364,941
[45] Date of Patent: Nov. 15, 1994

[54] 5-ACYL-4,5,6,7-TETRAHYDROTHIENO (3,2-C)PYRIDINE-2-CARBOXYLIC ACID DERIVATIVE AND PROCESS FOR PRODUCING THE SAME

[75] Inventors: Katsuyoshi Yamakawa; Kozo Sato, both of Minami-ashigara; Takashi Suginome, Odawara, all of Japan

[73] Assignee: Fuji Photo Film Co., Ltd., Kanagawa, Japan

[21] Appl. No.: 70,245

[22] Filed: Jun. 2, 1993

[30] Foreign Application Priority Data

Jun. 10, 1992 [JP] Japan .................. 4-150306

[51] Int. Cl.$^5$ .................. C07D 471/04; C07D 495/04
[52] U.S. Cl. .................. 546/114; 546/315
[58] Field of Search .................. 546/114

[56] References Cited

PUBLICATIONS

Chemical Abstracts, vol. 109, No. 13, Sep. 26, 1988, Columbus, Ohio, US, Abstract No. 110409s.

*Primary Examiner*—Alan L. Rotman
*Attorney, Agent, or Firm*—Sughrue, Mion, Zinn, Macpeak & Seas

[57] ABSTRACT

An intermediate, 5-Acyl-4,5,6,7-tetrahydrothieno [3,2-c ]pyridine- 2-carboxylic acid derivative of the following general formula (I):

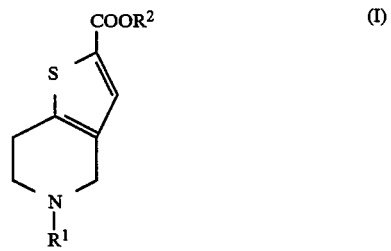

wherein $R^1$ represents an acyl group and $R^2$ represents a hydrogen atom or an alkyl group is useful for synthesizing ticlopidine hydrochloride from an inexpensive, easily available compound in short steps.

16 Claims, No Drawings

5-ACYL-4,5,6,7-TETRAHYDROTHIENO (3,2-C)PYRIDINE-2-CARBOXYLIC ACID DERIVATIVE AND PROCESS FOR PRODUCING THE SAME

BACKGROUND OF THE INVENTION

The present invention relates to new synthetic intermediates useful for producing ticlopidine hydrochloride having an effect of inhibiting platelet aggregation in an economical manner on an Industrial scale, and a process for producing them.

Reports were made from old times on the synthesis of a 4,5,6,7-tetrahydrothieno[3,2-c]pyridine skeleton of ticlopidine hydrochloride. The processes for the synthesis can be roughly divided into two processes. One is a process wherein a thiophene derivative is used as the starting material and a tetrahydropyridine ring is closed [see, for example, Japanese Patent Publication for Opposition Purpose (hereinafter referred to as "J.P. KOKOKU") No. Sho 56-2068, Japanese Patent Unexamined Published Application (hereinafter referred to as"J.P. KOKAI") No. Sho 62-103088 and EP 439404A2]and the other is a process wherein a piperidone derivative is used as the starting material and a thiophene ring is closed (see, for example, J.P. KOKAI Nos. Sho 63-2992 and Sho 63-126883, EP 360293A2 and DE 2,701,511). The reaction schemes of them are as follows:

Known reaction scheme 1:

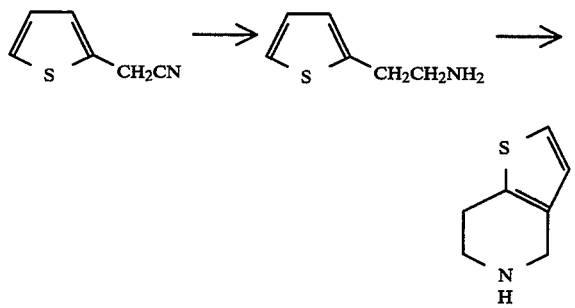

Known reaction scheme 2:

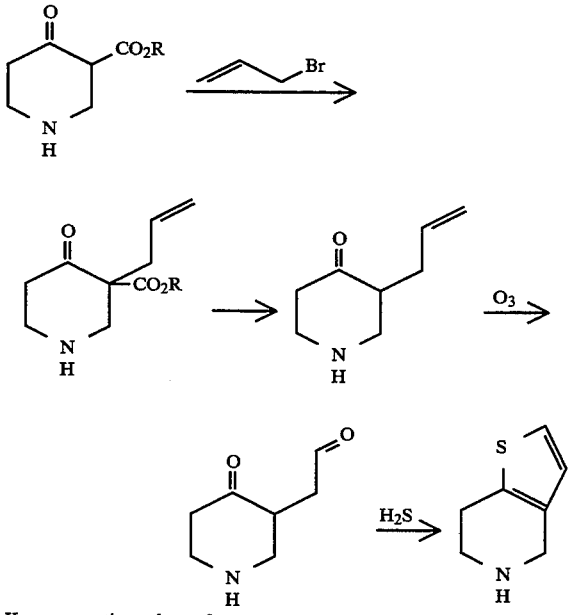

Known reaction scheme 3:

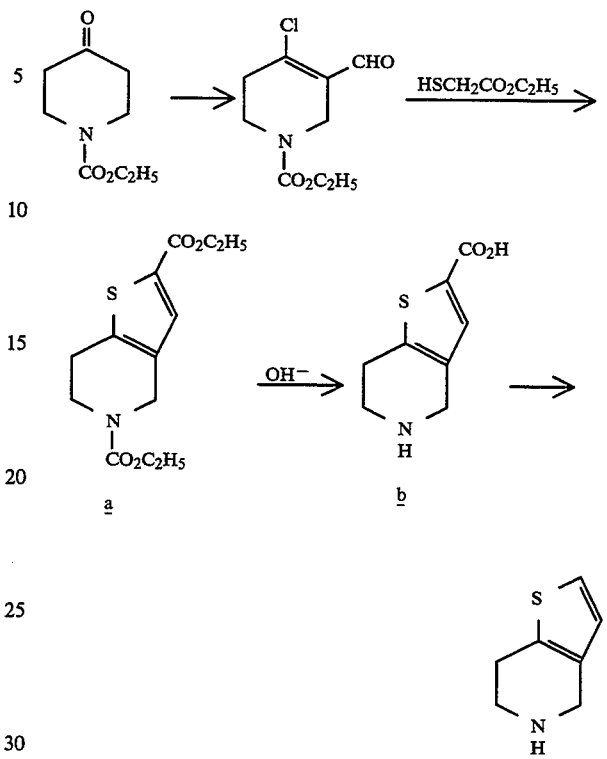

The known reaction schemes 1, 2 and 3 are disclosed in J.P. KOKAI No. Sho 62-103088, EP 360293A2 and J.P. KOKAI No. 63-2992, respectively. Although the known reaction scheme 1 comprising only a small number of the reaction steps is an advantageous process, a further improvement is demanded, since it has problems that a cyanide is used as the starting material and that side reactions occur in the course of the reduction. The investigations of the known reaction schemes 2 and 3 were started relatively recently and only a very small number of reports were proposed. Thus no process for producing the intended compound from an inexpensive starting material by short steps has been found yet.

SUMMARY OF THE INVENTION

The object of the present invention is to provide an intermediate useful for synthesizing ticlopidine hydrochloride from an inexpensive, easily available compound in short steps.

Another object of the present invention is to provide a process for producing an intermediate useful for synthesizing ticlopidine hydrochloride from an inexpensive, easily available compound in short steps.

These and other objects of the present invention will be apparent from the following description and Examples.

The first aspect of the present invention relates to 5-acyl4,5,6,7-tetrahydrothieno[3,2-c ]pyridine-2-carboxylic acid derivatives of the general formula (I):

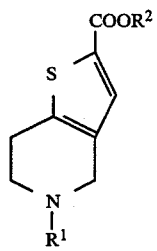 (I)

wherein R¹ represents an acyl group and R² represents a hydrogen atom or alkyl group.

The second aspect of the present invention relates to a process for producing compounds of the general formula (I) which comprises reacting a 5-acyl-3-amino-4,5,6,7-tetrahydrothieno[3,2-c]pyridine-2-carboxylic acid derivative of the general formula (II):

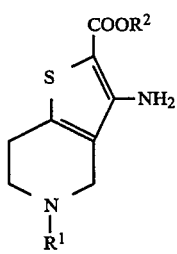 (II)

wherein R¹ and R² are as defined above with a nitrite under an acidic condition to form a diazonium salt and subjecting the diazonium salt to a reductive nitrogen-removing reaction.

DETAILED EXPLANATION OF PREFERRED EMBODIMENTS

The compounds of the general formula (I) are synthetic intermediates useful for producing ticlopidine hydrochloride by the following reaction scheme:

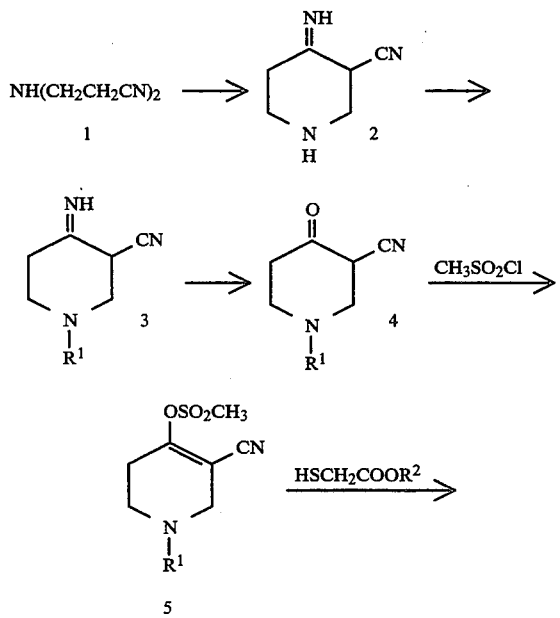

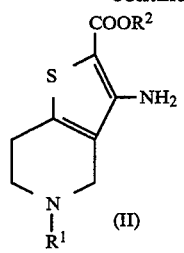

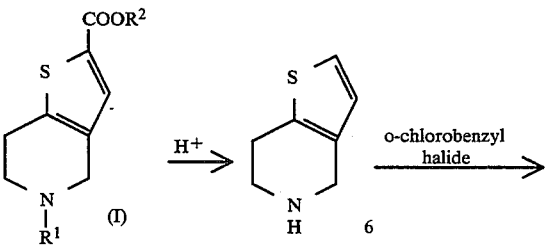

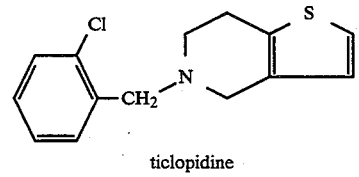

ticlopidine

Namely, a compound of the general formula (II) is synthesized from 3,3'-iminodipropionitrile 1 which is the starting material and easily available on the market at a low cost. This compound is deaminated (by diazotization and reduction) to easily obtain a compound of the general formula (I). Ticlopidine hydrochloride is produced by hydrolyzing and decarboxylating the deaminated compound under an acidic condition in one step to form a compound 6 and condensing it with an o-chlorobenzyl halide.

The compounds of the general formula (I) of the present invention are intermediates similar to the compound a in the above known reaction scheme 3 which has been known as an intermediate for ticlopidine hydrochloride. However, when the compound a is to be converted into the compound 6 by the known process 3, it is necessary to deamidate the compound a at a high temperature under a strong alkaline condition to form the compound b, and then decarboxylate the compound b with copper/quinoline or an acid. These successive two steps cannot be conducted in one step, since the properties of the liquids are opposite to each other. On the contrary, the compounds of the general formula (I) can be deamidated and decarboxylated at one time by only treating with an acid (such as hydrochloric acid, sulfuric acid or hydrobromic acid) without necessitating the treatment under the strong alkaline condition. Thus the Steps can be simplified by the present invention. Therefore, by using the compounds of the general formula (I) of the present invention, the amount of wastes formed in the course of the production of ticlopidine hydrochloride is reduced to reduce the cost and also to realize an extremely great merit in the prevention of environmental pollution.

The detailed description will be made on the compounds of the present invention hereafter.

R¹ in the above general formula (I) represents an acyl group having preferably 1 to 20 carbon atoms, more preferably 1 to 8 carbon atoms (such as formyl, acetyl, t-butylcarbonyl, benzoyl or o-chlorobenzoyl group). $R^2$ in the above general formula (I) represents a hydrogen atom or alkyl group. The alkyl groups include straight chain and branched alkyl groups having 1 to 20 carbon atoms, preferably 1 to 8 carbon atoms (such as methyl, ethyl, butyl and 2-ethylhexyl groups).

Examples of the compounds of the general formula (I) of the present invention are listed in Tables 1 and 2.

TABLE 1

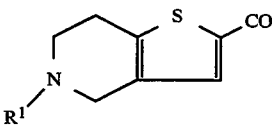 (I)

| No. | $R^1$ | $R^2$ |
|---|---|---|
| 1 | CHO— | $CH_3$— |
| 2 | " | $C_2H_5$— |
| 3 | " | $C_4H_9$— |
| 4 | " | $C_4H_9CH(C_2H_5)CH_2$— |
| 5 | " | H— |
| 6 | $CH_3CO$— | $CH_3$— |
| 7 | " | $C_2H_5$— |
| 8 | " | $C_4H_9$— |
| 9 | " | $C_4H_9CH(C_2H_5)CH_2$— |
| 10 | " | H— |
| 11 | $t-C_4H_9CO$— | $CH_3$— |
| 12 | " | $C_2H_5$— |
| 13 | " | $C_4H_9$— |
| 14 | " | $C_4H_9CH(C_2H_5)CH_2$— |
| 15 | " | H— |
| 16 | $\phi CO$— | $CH_3$— |
| 17 | " | $C_2H_5$— |

TABLE 2

Examples of the compounds of formula (I)

| No. | $R^1$ | $R^2$ |
|---|---|---|
| 18 | $\phi CO$— | $C_4H_9$— |
| 19 | " | $C_4H_9CH(C_2H_5)CH_2$— |
| 20 | " | H— |
| 21 | ![o-chlorobenzoyl] | $CH_3$— |
| 22 | " | $C_2H_5$— |
| 23 | " | $C_4H_9$— |
| 24 | " | $C_4H_9CH(C_2H_5)CH_2$— |
| 25 | " | H— |

The detailed description will be made on the process of the present invention hereafter.

The nitrites usable for forming the diazonium compounds include alkali nitrites such as sodium nitrite, potassium nitrite and lithium nitrite. In them, sodium nitrite is particularly preferred. The acids usable for the diazonium-forming reaction are not particularly limited so far as they are capable of liberating nitrous acid from the nitrite. They include, for example, hydrochloric acid, sulfuric acid, hydrobromic acid and acetic acid. In them, hydrochloric acid is particularly preferred. The solvents include water, alcohols, acetic acid, propionic acid, acetonitrile, THF, etc. They can be used either singly or in the form of a mixture of them. The above-mentioned acids for the diazonium-forming reaction can be used also as the solvent. Particularly preferred solvents are water, acetic acid, deluted sulfuric acid, etc.

The amount of the nitrite used is usually 0.9 to 2.0 mol, preferably 1.0 to 1.3 mol, per mol of the compound of the general formula (II), and the amount of the acid used is 2.0 to 20 mol, preferably 2.5 to 10 mol, per mol of the nitrite. When excess nitric acid remains in the reaction liquid after completion of the reaction, it can be decomposed by addition of sulfamic acid or urea. The reaction temperature is usually $-5°$ to $10°$ C., preferably $0°$ to $5°$ C. The reaction time which markedly varies depending on the kinds and relative amounts of the nitrite, acid used and the reaction temperature is usually to 3 hours, preferably 1 to 2 hours. After completion of the reaction, the diazonium salt can be isolated. Usually, however, the reaction product is subjected to the subsequent reaction without separation.

The reducing agents used for the nitrogen-removing reaction of the diazonium salt obtained as described above include hypophosphorous acid, formic acid, sodium formate, ammonium formate, hypophosphinous acid, sodium salt of hypophosphinous acid, hydrazine, formaldehyde, ethanol, etc. Further triethylsilane hydride, sodium borohydride, etc. are also usable. Hypophosphorous acid, formic acid, hypophosphinous acid, etc. are preferred, Metallic copper, copper salt, palladium, palladium salt, etc. are advantageously used as a catalyst for the reduction reaction. It is preferable that the catalyst is used in amount of 0.1 to 10 mol % of the reducing agent. The amount of the reducing agent is 1 to 100 mol, preferably 1 to 10 mol, per mol of the diazonium salt The reaction temperature is usually $-20$ to $+20°$ C., preferably $-10°$ to $+10°$ C. The reaction time which markedly varies depending on the variety and amount of the reducing agent used and reaction temperature is usually 0.5 to 5 hours, preferably 0.5 to 2 hours. After completion of the reaction, the intended product can be isolated by an ordinary method such as neutralization, extrusion, extraction, washing, concentration or crystallization. The product can be purified, if necessary, by recrystallization, column chromatography or the like.

In the compounds of the general formula (I) of the present invention produced as described above, those in which $R^1$ represents o-chlorobenzoyl group are converted into 5-o-chlorobenzoyi-4,5,6,7-tetrahydro-thieno[3,2-c]pyridine by only decarboxylation with copper/quinoline after completion of the alkali hydrolysis. This compound is a particularly useful intermediate, since it can be directly converted into ticlopidine by hydrogenating carbonyl oxygen of the benzoyl group without using any o-chlorobenzyl halide.

The compound of the general formula (II) used in this process can be easily synthesized from 3,3'-iminodipropionitrile 1 as described above. The details are as described below.

3,3'-iminodipropionitrile 1 is treated with a strong base (such as metallic sodium, sodium hydride or a sodium alkoxide) to obtain a ring-closed compound 2 [J. Am. Chem. Soc., 69, 1535 (1947)], which is then reacted with an acid halide or acid anhydride which leaves $R^1$ as the residue to form a compounds. The compound 3 is hydrolyzed with hydrochloric acid to obtain a 3-cyano-4-piperidone derivative 4. It is also possible to synthesize the compound 4 in one pot without isolating the compounds 2 and 3.

A compound 5 is produced from the 3-cyano-4-piperidone derivative 4 by reacting the compound 4 with methanesulfonyl chloride.

This reaction is conducted preferably in the presence of a base such as sodium methoxide, sodium carbonate, potassium carbonate, potassium t-butoxide, triethylamine, diazabicyclo[5,4,0]undecene (DBU), 2,6-lutidine, collidine or pyridine. Pyridine used as the base can act also as the solvent. The amount of the base used is usually 1 to 100 mol, preferably 1 to 10 mol and more preferably 1 to 1.5 mol, per mol of the compound 4.

The reaction temperature is usually 0° to 25° C., preferably 0 to 15° C. The reaction time which markedly varies depending on the molar ratio of the starting materials to be reacted and reaction temperature is usually 1 to 4 hours, preferably 1 to 2 hours.

After completion of the reaction, the reaction solution is poured into cold dilute hydrochloric acid, and the product is extracted with a suitable solvent and concentrated to isolate the compound 5 in the form of, for example, a colorless liquid. However, in the practical production, this product can be subjected to the subsequent reaction without isolation.

The solvents usable for the reaction for producing the compound 4 from the compound 1 or for producing the compound 5 from the compound 4 include, for example, acetonitrile, dimethylacetamide, dimethylformamide, dimethylimidazolidinone, tetrahydrofuran, diethyl ether, dioxane, benzene, toluene, xylene, ethanol, methanol, dichloromethane, chloroform and ethyl acetate.

Then a compound of the general formula (II) is produced from the compound 5 and thioglycolic acid or an ester thereof. The amount of thioglycolic acid or the ester thereof is 0.5 to 2 mol, preferably 0.9 to 1.2 mol, per mol of the compounds. The bases which can be present in the reaction system include, for example, sodium hydride, sodium methoxide, sodium carbonate, potassium carbonate, potassium t-butoxide, triethylamine and diazabicyclo[5,4,0]undecene (DBU). Particularly preferred bases are triethylamine, DBU, etc. These bases can be used either singly or in combination of two or more of them. The amount of the base is usually 1 to 10 mol, preferably 1 to 3 mol, per mol of the compound 5.

When thioglycolic acid is used instead of the thioglycolic ester, replacement reaction of —SH group of thioglycolic acid with —$OSO_2CH_{3s}$ group of the compound 5 is conducted by the treatment with the base in the same manner as that described above and then the resultant product is reacted with an alkylating agent in the presence of a base or, alternatively, thioglycolic acid is reacted with an alcohol in the presence of an acid catalyst to esterify the carboxyl group of thioglycolic acid and the resultant ester is treated with a strong base to conduct the ring-closing reaction, thereby forming a compound of the general formula (II). Examples of the alkylatinq agents include methyl iodide, dimethyl sulfate, diazomethane, ethyl orthoformate and ethyl orthoacetate. Examples of the alcohols include methanol, ethanol and 2-ethylhexanol. The acid catalysts used in the esterification with the alcohol include sulfuric acid. hydrochloric acid, aromatic sulfonic acids such as p-toluenesulfonic acid and Lewis acids such as boron fluoride etherate. The reaction temperature is usually 0° to 25° C , preferably 0° to 15° C . The reaction time which markedly varies depending on the molar ratio of the starting materials and reaction temperature is usually 1 to 4 hours, preferably 1 to 2 hours.

After completion of the reaction, the intended product can be isolated by an ordinary method such as neutralization. extrusion, extraction, washing, concentration or crystallization. The product can be purified, if necessary, by recrystallization, column chromatography or the like.

EXAMPLES

EXAMPLE 1

Compound No. 16

7.91 g (0,025 mol) of methyl 3-amino-5-benzoyl-4,5,6,7-tetrahydrothieno[3,2-c]pyridine-2-carboxylate was dissolved in 31 ml of 75% sulfuric acid. The internal temperature was lowered to −5° C. An aqueous solution of 3.45 g (0.05 mol) of sodium nitrite in 15 ml of water was slowly added dropwise to the solution while the internal temperature was kept at 0° or below and then the mixture was stirred at 0° or below for 30 min. 100 ml of 50% aqueous hypophosphorous acid solution was cooled to an internal temperature of 0° C. or below and the reaction solution obtained as described above was added dropwise to this solution. The resultant mixture was stirred at an internal temperature of 0° C. or below for about 1 hour. The mixture was further stirred until foaming ceased for 3 to 4 hours while the internal temperature was slowly elevated to room temperature.

After completion of the reaction, the mixture was neutralized (pH ~ 5) by addition of an aqueous potassium carbonate solution. After extraction with ethyl acetate (100 ml ×2), the ethyl acetate layer was washed with water and dried over sodium sulfate. Ethyl acetate was distilled off under reduced pressure and the product was purified by column chromatography (n-hexane / ethyl acetate =2/1; silica gel) to obtain 6.93 g of methyl 5-benzoyl-4,5,6,7-tetrahydrothieno[3,2c]pyridine-2-carbonylate in the form of a colorless liquid. Yield: 92%.

From the following results of the determination of NMR spectrum, it was supposed that the product was a mixture of two amide bond rotational isomers A and B (A:B =1:1.5).

$^1$H-NMR (200 MHz), $\delta$ppm (CDCl$_3$, room temp.):

A 2.95(bs, 2H), 3.86(s, 3H), 4.08(bs, 2H), 4.53(bs, 2H), 7.43(s, 6H).

B 2.95(bs, 2H), 3.70(s, 2H), 3.86(s, 3H), 4.79(bs, 2H), 7.43(s, 6H).

EXAMPLE 2

Compound No. 8

Compound 8 was synthesized in the same manner as that of Example 1. It was in the form of a solid. From the following results of the determination of NMR spectrum, it was supposed that the product was a mixture of two amide bond rotational isomers A and B (A:B =Melting point: 60° to 63° C.

$^1$H-NMR (200 MHz), $\delta$ppm (CDCl$_3$, room temp.):

A 0.96(t, 3H, J=7.7Hz), 1.43(tq, 2H, J=7.7, 7.7Hz}, 1.71(tt, 2H, J=7.7, 7.7Hz), 2.17(s, 3H), 2.89(t, 2H, J=6.7Hz), 3.90(t, 2H J=6.7Hz), 4.26(t, 2H, J=7.7Hz), 4.55(s, 2H), 7.50(s, 1H)

B 0.96(t, 3H, J=7.7Hz), 1.43(tq, 2H, J=7.7, 7.7Hz), 1.71(tt, 2H, J=7.7, 7.7Hz), 2.20(s, 3H), 2.95(t, 2H, J=6.7Hz), 3.75(t, 2H J=6.7Hz), 4.26(t, 2H, J=7.7Hz), 4.66(s, 2H), 7.50(s, 1H).

EXAMPLE 3

Compound No. 20

Compound 20 was synthesized in the same manner as that of Example 1. From the following results of the determination of NMR spectrum, it was supposed that the product was a mixture of two amide bond rotational isomers A and B (A:B =1:1).

Colorless liquid

Mass spectrum <DI-EI, 70eV): 287(M+),182(M +-coph), 167,154,137,122, 105, 77.

1H-NMR (200 MHz), δppm (CDC13 , room temp.):
A2.97(bs, 2H), 4.08(bs, 2H), 4.55(bs, 2H), 7.49(s, B2.97(bs, 2H), 3.72(bs, 2H), 4.81(bs, 2H), 7.49(s, 6H)

EXAMPLE 4

Compound No. 21

Compound 21 was synthesized in the same manner as that of Example 1. From the following results of the determination of NMR spectrum, it was supposed that the compound was a mixture of two amide bond rotational isomers A and B (A:B =1:1.6). Colorless liquid 1H-NMR (200 MHz), δppm (CDCl3,room temp.):
A 3.04(t, 2H, J=6.0Hz), 3.56(t, 2H, J=6.0Hz), 3.84(s, 3H), 4.25(d , 1H, J=16.0Hz), 4.38(d, 1H, J=16.0Hz), 7.34(s, 1H), 7.49(m, 4H)

B 2.88(m, 2H), 3.09(s, 3H), 4.08(m, 2H), 4.79(d, 1H, J=17.0Hz ), 4.94(d, 1H, J=17.0Hz), 7.49(m, 4H), 7.58(s, 1H)

EXAMPLE 5

Compound No. 8

5.95 g of butyl 3-amino-5-acetyl-4,5,6,7-tetrahydrothieno[3,2-c]pyridine-2-carboxylate was dissolved in mixture of 15 ml of 80 % sulfuric acid and 20 ml of acetic acid. The internal temperature was lowered to 0 ° C . An aqueous solution of 2.07 g of sodium nitrite in 6 g of water was added dropwise to the solution at an internal temperature of 0° to 3° C. and then the mixture was stirred at 3° to 4 ° C. for 30 min.

2.0 g of sulfamic acid was added to the solution. After stirring the mixture until foaming ceased, the reaction mixture was slowly poured into mixture of 20 ml of 98% formic acid, 10 ml of water and 0.5 g of copper powder at a temperature of 3 to 6° C . The resultant mixture was stirred at the same internal temperature for t hour. The mixture was further stirred until foaming ceased while the internal temperature was slowly elevated to room temperature.

After completion of the reaction, the mixture was neutralized (pH=5) by addition of an aqueous sodium carbonate solution. After extraction with ethyl acetate (60 ml ×2), the ethyl acetate was distilled off under reduced pressure and the product was purified by column chromatography (n-hexane / ethyl acetate =1/1; silica gel) to obtain 4.95 g of butyl 5-acetyl-4,5,6,7-tetrahydrothieno[3,2-c]pyridine2-carbonylate in the form of a colorless crystal. Yield: 88%.

EXAMPLE 6

Compound No. 8

The same manner as that of Example 5 was repeated except that 20 g of mixture of formic acid and 50% hypophosphorous acid (1:1) was used instead of the mixture of 98% formic acid, water and copper. 5.1 g of compound No. 8 was obtained. Yield: 90%.

EXAMPLE 7

Compound No. 8

The same manner as that of Example 5 was repeated except that mixture of 50% hypophosphorous acid and 0.5 g of copper powder was used instead of the mixture of 98% formic acid, water and copper. 4.81 g of compound No. 8 was obtained. Yield: 86%.

What is claimed is:

1. A compound of the general formula (I):

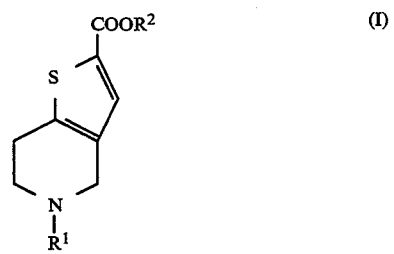

wherein $R^1$ represents an acyl group and $R^2$ represents a hydrogen atom or an alkyl group.

2. The compound according to claim 1 wherein $R^2$ is an alkyl group.

3. The compound according to claim 2 wherein $R^1$ is an acyl group having to 20 carbon atoms and $R^2$ is an alkyl groups having 1 to 20 carbon atoms.

4. The compound according to claim. 3 wherein $R^1$ is an acyl group having 1 to 8 carbon atoms.

5. The compound according to claim 3 wherein $R^2$ is an alkyl groups having 1 to 8 carbon atoms.

6. The compound according to claim 2 wherein $R^1$ is an acyl group having to 8 carbon atoms and $R^2$ is an alkyl groups having 1 to 8 carbon 7. A process for producing a compound of the general formula (I):

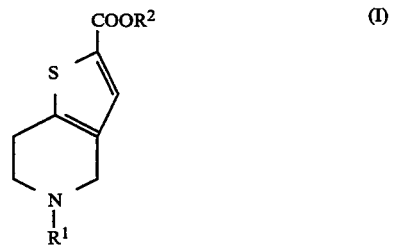

wherein $R^1$ represents an acyl group and $R^2$ represents a hydrogen atom or an alkyl group which comprises reacting a compound of the general formula (II):

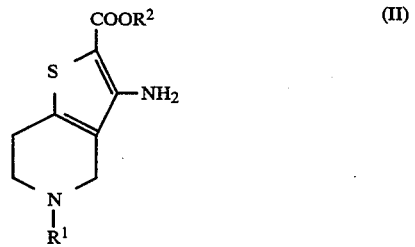

wherein $R^1$ and $R^2$ are as defined above with a nitrite under an acidic condition to form a diazonium salt and subjecting the diazonium salt to a reductive nitrogen-removing reaction.

8. The process according to claim 7 wherein $R^2$ is an alkyl group.

9. The process according to claim 8 wherein $R^1$ is an acyl group having 1 to 20 carbon atoms and $R^1$ is an alkyl groups having 1 to 20 carbon atoms.

10. The process according to claim 9 wherein $R^1$ is an acyl group having 1 to 8 carbon atoms.

11. The process according to claim 9 wherein $R^2$ is an alkyl groups having 1 to 8 carbon atoms.

12. The process according to claim 7 wherein $R^1$ is an acyl group having 1 to 8 carbon atoms and $R^2$ is an alkyl groups having 1 to 8 carbon atoms.

13. The process according to claim 7 wherein the amount of the nitrite is 0.9 to 2.0 mol per mol of the compound of the general formula (II).

14. The process according to claim 7 wherein the acid used for the diazonium-forming reaction is hydrochloric acid, sulfuric acid, hydrobromic acid or acetic acid and the amount of the acid is 2.0 to 20 mol per mol of the nitrite.

15. The process according to claim 7 wherein the reductive nitrogen-removing reaction is carried out using hypophosphorous acid, formic acid or hypophosphinous acid as a reducing agent.

16. The process according to claim 12 wherein the amount of the nitrite is 0.9 to 2.0 mol per mol of the compound of the general formula (II), the acid used for the diazonium-forming reaction is hydrochloric acid, sulfuric acid, hydrobromic acid or acetic acid, the amount of the acid is 2.0 to 20 mol per mol of the nitrite, and the reductive nitrogen-removing reaction is carried out using hypophosphorous acid, formic acid or hypophosphinous acid as a reducing agent.

* * * * *